United States Patent [19]

Ehrich et al.

[11] 4,248,632
[45] Feb. 3, 1981

[54] SOLUTION AND PROCESS FOR THE ACTIVATION OF SURFACES FOR METALLIZATION

[75] Inventors: Hans J. Ehrich; Wolfgang Clauss; Hartmut Mahlkow, all of Berlin, Fed. Rep. of Germany

[73] Assignee: Schering Aktiengesellschaft, Berlin and Bergkamen, Fed. Rep. of Germany

[21] Appl. No.: 11,847

[22] Filed: Feb. 13, 1979

Related U.S. Application Data

[63] Continuation of Ser. No. 814,133, Jul. 8, 1977, abandoned, which is a continuation-in-part of Ser. No. 416,735, Nov. 19, 1973, abandoned, which is a continuation of Ser. No. 232,505, Mar. 7, 1972, abandoned.

[30] Foreign Application Priority Data

Mar. 30, 1971 [DE] Fed. Rep. of Germany ....... 2116389

[51] Int. Cl.$^3$ .............................................. C23C 3/02
[52] U.S. Cl. .................................... 106/1.11; 204/30; 427/304

[58] Field of Search ............................ 106/1.05, 1.11; 427/304, 305, 306, 98; 204/30

[56] References Cited

U.S. PATENT DOCUMENTS

| 3,523,874 | 8/1970 | Dey ........................................ 204/30 |
| 3,650,708 | 3/1972 | Gallagher .............................. 204/30 |

FOREIGN PATENT DOCUMENTS 7204414  10/1972  Netherlands ........................... 106/1.11

Primary Examiner—Lorenzo B. Hayes
Attorney, Agent, or Firm—Michael J. Striker

[57] ABSTRACT

An activating agent for application to the unactivated surface of an organic polymer to prepare the surface for chemical metallization comprises an aqueous solution of (a) a water soluble metal salt of an inorganic acid, the metal being silver, gold, or a platinum group metal, and (b) an amount of a ligand-forming organic nitrogen compound sufficient to form a water soluble coordination complex with the metal salt, the solution having a pH between 2.2 and 7, the metal concentration being between about 0.1 and about 1 gram per liter.

2 Claims, No Drawings

SOLUTION AND PROCESS FOR THE ACTIVATION OF SURFACES FOR METALLIZATION

CROSS-REFERENCE TO RELATED APPLICATION

This is a continuation of application Ser. No. 814,133, filed July 8, 1977, which in turn is a continuation-in-part of Ser. No. 416,735, filed Nov. 19, 1973, and both now abandoned, and which in turn was a continuation of Ser. No. 232,505, filed Mar. 7, 1972, now abandoned.

BACKGROUND OF THE INVENTION

The invention relates to a solution for the coating of and activation of non-conductive surfaces for subsequent chemical metallization and also for the galvanic reinforcement of this coating, and to a process of metallization using such solutions.

The metallization of, in particular, non-conductive surfaces is known to require a pretreatment, for which several methods have already become known.

Thus, surfaces are treated, after their pickling with chromosulfuric acid, with solutions of palladium chloride, platinum chloride or gold chloride and then with a reducing solution for reducing the precious metal ions to metal.

According to another method, colloidal precious metal solutions are used, which already catalyze the surfaces without subsequent reduction.

On the surfaces catalyzed by these methods, it is then possible to deposit without the use of current, adhesive metal coatings by further treatment with metal salt solutions and action of a reducing agent.

These methods of metallization serve predominantly for the production of printed circuits and dielectric supports, and are therefore of great importance in the electrical industry.

A disadvantage of the known methods, however, for example, consists in that, when using palladium chloride as previous metal salt and tin-II chloride as reducing agent separately, only the activation of so-called non-coated, i.e. copper-metal free, support material is possible, for otherwise the precious metal would precipitate from the solution.

Activating solutions containing both the precious metal salt and the reducing agent, on the other hand, involve the disadvantage of a special sensitivity to impurity ions and other impurities, resulting in an irreversible coagulation of the precious metal.

GENERAL DESCRIPTION OF THE INVENTION

With the above in view, it is the object of the invention to develop a stable activating solution which in the presence of copper metal and less precious metals does not lead to precipitation of the precious metal and is insensitive to impurity ions and other impurities.

This problem is solved according to the invention by the use of a solution characterized by a content of at least one complex compound of a precious metal of the First or Eighth Subgroup of the Periodic Table of Elements with an N-containing compound.

As such complex compounds as an example there may be used, those of the general formula

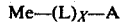

Me—(L)$_x$—A wherein Me is a precious metal of the First or Eighth Subgroup of the Periodic Table of Elements, L is an N-containing inorganic or organic radical, X an integer of at least 1, preferably 2 to 4, and A an inorganic or organic acid radical. In this formula, Me is preferably silver, gold, palladium, platinum, osmium, iridium and rhodium.

It is to be noted that the bond between the metal and the ligands is coordinative. The valence of the metals in the complex are preferably as follows: $Ag^+$, $Au^{+++}$, $Pd^{++}$, $Pt^{++}$, $Os^{6+}$, $Os^{8+}$, $Ir^{4+}$ and $Rh^{+++}$.

Specifically there may be named as N-containing ligands L for example: Ammonia as well as primary, secondary and tertiary amines.

As such there enter into consideration for example: Aliphatic or cycloaliphatic mono-, di- or poly-amines as well as their hydroxy, carboxy, sulfo and/or phosphoryl derivatives, aromatic mono-, di- or poly-amines or their hydroxy, carboxy, sulfo and/or phosphoryl derivatives, heterocyclic mono-, di- or poly-amines or their hydroxy, carboxy and/or sulfo derivatives, as well as N-containing mono- or multi-nuclear heterocyclic compounds or their hydroxy, carboxy and/or sulfo derivatives. These amines and their derivatives may be substituted by radicals, such as for example the alkyl or nitrilo group, etc.

As examples of such amines there may be named: Ammonia, methylamine, ethylamine, propylamine, butylamine, ethylene diamine, propylene diamine, isopropylene diamine, tetramethylene diamine, octamethylene diamine, piperidine, piperazine, pyrrolidine, benzylamine, diethylene triamine, ethylene diamine tetra-acetic acid, butylene diamine tetra-acetic acid, hexamethylene diamine tetra-acetic acid, octamethylene diamine tetra-acetic acid, nitrilotriacetic acid, iminodiacetic acid, ethylene diamine-N,N'-dipropionic acid, hexamethylene diamine-N,N'-dipropionic acid, ethylenediamine-tetrakis-isopropanol, ethylene-diamine-tetrakis-ethanol, triethanolamine, ethanolamine, o-phenyl-diamine, aniline, toluidine, triethylamine, tributylamine, N,N,N',N'-tetramethyl-ethylene-diamine, N,N'-dimethyl-ethylenediamine, N,N-dimethyl-ethylenediamine, N-methyl-ethylenediamine, diethylamine, dibutylamine.

Imidazole, 1-methyl-imidazole, 1-propyl-imidazole, 2,4-di-methyl-imidazole, 4-methyl-imidizole, 2-isopropyl-imidazole, 2-phenyl-imidazole, 1-benzylimidazole, β-imidazolopropionic acid, 1,2-dimethyl-imidazole, 1-methyl-2-hydroxymethyl-imidazole, 4-sulfo-imidazole, 2-methyl-4-sulfo-imidazole, 2-(sulfophenyl)-imidazole, 2-isopropyl-4-sulfo-imidazole, 1-n-propyl-5-sulfo-imidazole, 1-n-propyl-4-sulfo-imidazole, 1,2-bis-(1'-imidazolyl)-ethane, 1-(p-sulfophenyl)-imidazole, histidine, 2-(imidazolo-ethyl)-pyridine, 1-(2'-aminoethyl)-imidazole-hydrochloride, 1-(3'-aminopropyl)-imidazole-hydrochloride, 1-methyl-2-carboxy-methyl-imidazole, 2-(p-sulfophenyl)-4-sulfo-imidazole, 1-methyl-2-sulfo-imidazole, 2-sulfoimidazole, 1,2-bis-(1'-methyl-5'-imidazolyl)-ethane, 5-sulfo-benzimidazole, 5,7-disulfobenzimidazole, 1,2-bis-(5'-(5'-sulfobenzimidazolyl-(2'))-ethane, 1,4-bis-(5'-sulfobenzimidazolyl-(2'))-butane, polyvinylimidazole (CDP=2 to 500), polyallylimidazole (CDP=2 to 500), 3,5-dimethylpyrazole, 4-sulfopyrazole, 1-methylpyrazole, 3-methylpyrazole, 1,3-dimethyl-pyrazole, 1-phenylpyrazole, 1-carboxymethyl-pyrazole, 1-carboxy-ethyl-pyrazole, 1-aminoethyl-pyrazole-hydrochloride, 1-aminopropyl-pyrazole-hydrochloride, 3,3'-dipyrazolyl, 1,3-dimethyl- 5-hydroxy-pyrazole, 1-phenyl-3-methyl-5-hydroxy-pyrazole, 1-(p-sulfophenyl)-3-methyl-5-hydroxy-pyrazole, 1-(m-sulfophenyl)-3-methyl-5-hydroxy-pyrazole, 1-(p-aminophenyl)-3-methyl-5-hydroxy-pyrazole, 1-(p-chlorphenyl)-3-methyl-5-hydroxy-pyrazole, 1-(p-sulfophenyl)-3-carboxy-5-hydroxy-pyrazole, 1,2-bis-(1'-pyrazolyl)-ethane, 7-sulfo-benz-pyrazole, 1-carboxyethyl-benzyprazole, 1,2-bis-(3'-pyrazolyl-ethane, di-(3-pyrazolyl)-methane.

Pyridine, 2-aminopyridine, 3-aminopyridine, 4-aminopyridine, 2-hydroxypyridine, 3-hydroxypyridine, 4-hydroxypyridine, 2,6-diaminopyridine, 2,3-diaminopyridine, 3,4-diaminopyridine, 2-aminomethyl-pyridine, 3-aminomethyl-pyridine, 4-aminomethyl-pyridine, 4-picoline, 3-picoline, 2-picoline, 2,6-lutidine, 2,4-lutidine, 3-pyridinsulfonic acid, 2,2'-dipyridyl, 4,4'-dipyridyl, 1,2-di-(2'-pyridyl), 2,2'-dipyridylmethane, 2,2'-dipyridyl-amine, 1,2-dihydroxy-1,2-di-(2'-pyridyl)-ethane. 2,2'-dipyridyl-ethylene, 4,4'-dipyridyl-ethylene, 3-sulfo-3,3'-dipyridyl, 1,2-di-(4'-pyridyl)-ethane.

2-amino-pyrimidine, 2,4,6-triamino-pyrimidine, 1,4-dimethyl-pyrimidine, 1,5-dimethyl-pyrimidine, 4,5-dimethylpyrimidine, 4,6-dimethylpyrimidine, 2,4-bis-(diethylamino)-pyrimidine, 3,6-bis-(dimethylamino)-pyrimidine, 3,6-bis-(ethylamino)-pyrimidine, 2-hydroxypyrimidine, 4-hydroxypyrimidine, 4,6-dihydroxypyrimidine, barbituric acid, cytosine, pyrimidine, bis-(2-methyl-4-pyrimidyl), 2,2'-dipyrimidyl, 4,4'-dipyrimidyl, uracil, 5-methyl-cytosine, 2-methyl-pyrimidine, 2-ethyl-pyrimidine, 2-phenyl-pyrimidine, 2-amino-6-ethyl-pyrimidine, 2-amino-6-methyl-pyrimidine, 2-amino-5-pyrimidine, 2-amino-4-hydroxy-pyrimidine, 2-carboxy-pyrimidine, 5-carboxymethyl-pyrimidine, 2-carboxymethyl-5,6-dimethyl-pyrimidine, 2-methyl-5-carboxymethyl-pyrimidine, pyridazine, 3-methyl-pyridazine, pyrazine, 2,3,5,6-tetramethyl-pyrazine, 2,5-dimethyl-6-hydroxy-pyrazine, 2-hydroxy-pyrazine, 2-amino-pyrazine.

Urotrophine, 2,6-diamino-4-methyl-triazine-(1,3,5), 2,6-diamino-4-ethyl-triazine-(1,3,5), 2,6-diamino-4-propyl-triazine-(1,3,5), 2,6-diamino-4-carboxymethyl-triazine-(1,3,5), 2,6-diamino-4-carboxyethyl-triazine-(1,3,5), 2,6-diamino-4-sulfopropyl-triazine-(1,3,5), melamine, cyanuric acid; 2,4,6-tris-methyl-amino-triazine-(1,3,5), 2,4,6-tris-ethylamino-triazine(1,3,5), 2,4,6-tris-diethylamino-triazine-(1,3,5), bis-(4,6-diamino-2-triazinyl-(1,3,5))-methane, 1,2bis-(4',6'-diamino-triazinyl-(1',3',5'))-ethane, 1,3-bis-(4',6'-diamino-2'-triazinyl-(1',3',5'))-propane, 1,2-bis-(4',6'-diamino-triazinyl-2'-amino)-ethane, 2,4-diamino-triazine-(1,3,5), 2,4-diamino-6-(p-sulfophenyl)-triazine-(1,3,5), 2,4-diamino-6-ethyl-triazine-(1,3,5), 2,4-dihydroxy-6-methyl-triazine-(1,3,5), cyanuric acid-hydroxyethylester, 2,4-dihydroxy-6-carboxymethyl-triazine-(1,3,5), 2-amino-4-carboxy-methyl-6-n-butylamino-triazine (1,3,5), 2-amino-4-carboxy-6-n-butylamino-triazine-(1,3,5), 2-amino-4-carboxyethyl-6-n-butylamino-triazine-(1,3,5), 2-amino-4-hydroxy-triazine-(1,3,5), 3-amino-triazine-(1,2,4), 3-amino-5, 6-dimethyl-triazine-(1,2,4), 4-hydroxy-5,6-dimethyl-triazine-(1,2,4), 4-hydroxy-5-phenyl-triazine-(1,2,4), triazine-(1,2,4), 3,3'-bis-(5,6-dimethyl-triazine)-(1,2,4), 3,5-dihydroxy-triazine-(1,2,4), 3,5dihydroxy-6-methyl-triazine-(1,2,4), 3,5-hydroxy-6-butyl-triazine-(1,2,4), 3,5-hydroxy-6-phenyl-triazine-(1,2,4), 3,5-dihydroxy-6-carboxypropyl-triazine-(1,2,4).

Triazol-(1,2,4), 4-ethyl-triazole-(1,2,4),4-methyl-triazole-(1,2,4), 4-phenyl-triazole-(1,2,4), 3,4,5-trimethyl-triazole-(1,2,4), 4-(p-sulfophenyl)-triazole-(1,2,4), 3-methyl-triazole-(1,2,4), 3-ethyl-triazole-(1,2,4), 3,5-dimethyl-triazole-(1,2,4), 3-phenyl-triazole-(1,2,4), 1-methyl-triazole-(1,2,4), 1-ethyl-triazole-(1,2,4), 1-phenyl-triazole-(1,2,4), 3-sulfo-triazole-(1,2,4), 3-amino-triazole-(1,2,4), 3,5-diamino-triazole-(1,2,4), 1,2-bis(5'-sulfo-3'-triazolyl)-ethane, 1,2-bis-(5'-amino-3'-triazolyl)-ethane, 1,2-bis-(3'-triazolyl)-ethane, 1,2-bis-(4'-methyl-3'-triazolyl)-ethane, bis-(3-triazolyl)-methane, bis-(5-sulfo-3-triazolyl)-methane, bis-(5-amino-3-triazolyl)-methane,bis-(3-triazolyl)-methane, bis-(5-sulfo-3-triazolyl), bis-(5-amino-3-triazolyl), 3,3'-bis-triazolyl, 1,2-bis-(1'-triazolyl)-ethane, 3-(2'-aminoethyl)-triazole-(1,2,4), β-(1-triazolyl)-propionic acid, 1,4-bis-(5'-sulfo-3'-triazolyl)-butane, 1,4-bis-(5'-amino-3'-triazolyl)-butane, 1-(3-sulfopropyl)-triazole-(1,2,4), 1,2-bis-(4'-triazolyl)-ethane, 1-methyl-triazole-(1,2,3), 1-ethyl-triazole-(1,2,3), 2-ethyl-triazole-(1,2,3), 2-propyl-triazole-(1,2,3), 1-(2'-carboxyethyl)-triazole-(1,2,3), 5-sulfo-benzotriazole, 5,7-disulfo-benzotriazole, benzotriazole, 4-methyl-triazole-(1,2,3), 4,5-dimethyl-triazole-(1,2,3), 4-butyl-triazole-(1,2,3,), 4-phenyl-triazole-(1,2,3), 1-(3'-aminopropyl)-triazole-(1,2,3), 1-(2'-aminoethyl)-triazole-(1,2,3), 1,2-bis-(1'-triazole)-ethane.

Pyrrole, 1-methyl-pyrrole, 1-ethyl-pyrrole, 1-(2-carboxyethyl-pyrrole, 2-methyl-pyrrole, 2,5-dimethyl-pyrrole, di-(2-pyrrolyl)-methane, di-(1-methyl-2-pyrrolyl)-methane, 2-ethyl-pyrrole, tryptophane.

Polyethylenimine, N,N-dimethyl-polyvinylamine, polyvinylimidazole, polyallylimidazole, polyvinylpyridine, polyvinylpyrrolidone, polyvinylmorpholine, polyvinylmorpholinone, polyvinyl-5-alkyl-oxazolidone, N-polyvinyl-N,N'-ethylene-urea, soy proteins, albumins.

For complex salt formations that are suitable are any desired inorganic and organic acid radicals A, such as the chloride radical ($Cl^-$), the sulfate radical ($SO_4^{--}$), the phosphate radical ($PO_4^{3--}$), the nitrate radical ($NO_3^-$), the perchlorate radical ($ClO_4^-$), the acetate radical ($CH_3COO^-$), the propionate radical ($CH_3-CH_2-COO^-$) and the oxalate radical $[(COO^-)_2]$.

The activating solutions, according to the invention, contain precious metal thus complexed in concentrations of about 0.05 g/liter (referred to the precious metal) up to the respective solubility limit, preferably from 0.1 to 1 g/liter.

The pH value of the activating solution of the present invention is critical and must be non-alkaline, ranging from fairly strong acidity to neutral, said range being from 2.2 to 7.

It has proved particularly advantageous if an increase in the absorption of the precious metal complex on the plastic is desired that the solution contain also a water-soluble polymeric orgaic compound, preferably soy protein or polyethyleneimine, in a concentration of about 0.1 g/liter up to the solubility limit.

If the high-polymeric compound has available N-containing ligand for the complexing of precious metals, it can replace the above-mentioned low-molecular complexes and possible combine the property of adsorption increase with that of complex formation.

Naturally, these high-molecular N-containing compounds do not form homogeneous complex compounds. For their production at least a molar ratio of metal to the N-containing compound is chosen as the maximum coordination number of the precious metal to the number of "n" monomer units which have available a N ligand.

U.S. Pat. No. 3,523,874 relates to the metal coating of aromatic polymers, and in order to render the polymer surface susceptible to plating, it is contacted with nitric acid or other nitration agent which forms nitro groups on the polymer. Thereafter the nitrated surface is treated with a reducing agent to reduce the nitro groups to amino groups, then with a diazotizing agent followed by coupling with a phenolic coupling agent to form an azo compound on the polymer surface. The thus treated surface is contacted with a complex of a metal salt capable of reacting therewith. The complex may be that of silver, gold or palladium, with an amine, pyridine or quinoline, to produce a solution having a basic pH above 7, preferably 10–13, i.e. alkaline.

In contrast thereto, the activating compositions of the present invention are predominantly of an acidic pH, because they are intended to be applied directly to the polymer surface which has not been previously activated (or chemically treated), in order to activate the polymer surface.

The complex compounds to be used according to the invention can be produced in the usual well known manner, such as described in the following illustrative examples. These examples are not however to be regarded as limiting the invention thereto:

1. Complexes with palladium (a) Dichloro-2,2'-dipyridyl-palladium-(II)[Pd $(C_5H_4N-C_5H_4N)$ $Cl_2$] is formed from 0.5 g dipyridyl in 30 ml alcohol and 0.9 g $(NH_4)_2PdCl_4$ in 10 ml water and 50 ml alcohol by heating. From this solution crystals of the desired compound separate upon cooling.

(b) Dichloro-bis-(2-aminopyridine)-palladium-(II)[Pd $(C_5H_4N-NH_2)$ $Cl_2$] and dichloro-tetrakis-(2-aminopyridine)-palladium-(II) $(Pd(C_5H_4N-NH_2)_4Cl_2'$ respectively are formed by combining a concentrated aqueous solution of $K_2PdCl_4$ with 2 or 4 moles of 2-aminopyridine.

2. Complexes with platinum (c) Dichloro-dipyridine-platinum-(II)[Pt$(C_5H_5N)_2$ $Cl_2$]: A solution of 10 g of pure $K_2PtCl_4$ in 100 ml of cold water is mixed with a solution of 3.7 g of pyridine in 25 ml water and left standing for 24 hours; the precipitate formed is washed with cold water and dried in air.

(d) Dichloro-tetrapyridine-platinum-(II)[Pt $(C_5H_5N)_4Cl_2$] is produced by heating Pt$(C_5H_5N)_2Cl_2$ over excess pyridine and subsequent evaporation of the solution at room temperature.

(e) Dichloro-bis-(2-aminopyridine)-platinum-(II) [Pt $(C_5H_4-NH_2)_2Cl_2$]: A solution of $K_2PtCl_4$ (1 mole) is mixed with little water with exactly 2 mole 2-aminopyridine in aqueous solution. After two to three hours, the compound starts to separate out as a yellow to yellow-green precipitate. The precipitate is washed with little water.

(f) Dichloro-tetrakis-(2-aminopyridine)-platinum-(II) [Pt $(C_5H_4-NH_2)_4Cl_2$]: For its preparation, dichloro-bis-(2-amino-pyridine)-platinum-(II) is treated with excess 2-aminopyridine in little water and heated on the waterbath for 5 to 6 hours. After concentration to a small volume, the desired compound separates out gradually.

3. Complexes with Rhodium (g) Trichloro-tri-pyridine-rhodium-(III) [Rh$(C_5H_5N)_3Cl_3$]: For its preparation, 3 g of $Na_3RhCl_6\times 12$ $H_2O$ and 2.4 g of pyridine are heated with 12 ml of water on the waterbath. The oil separating out at first crystallizes through, slowly. The crystals can be purified by recrystallization from alcohol. If the tripyridine compound is heated in pyridine for a prolonged time, trichloro-tetrapyridine-rhodium-(III) is obtained.

4. Complexes with Ruthenium (h) Dichloro-tetrapyridine-ruthenium-(III) [Ru$(C_5H_5N)_4Cl_2$] is formed by boiling ammonium chloro-ruthenate-(III) in pyridine for several hours. Upon cooling, yellow crystals crystallize out.

5. Complexes with Iridium (i) Trichloro-tripyridine-iridium-(III) [Ir$(C_5H_5N)_3Cl_3$]: For its preparation, KIr $(C_5H_5N)_2Cl_4$, which can be obtained from pyridine/$H_2O$ and $K_3IrCl_6\times 3$ $H_2O$, is heated on the waterbath in puridine for several hours. The yellow crystals separate out slowly during the reaction.

6. Complexes with Osmium (k) Perchlorato-tri-2,2'-dipyridine-osmium-(II) [Os $(C_5H_4N-C_5H_4N)_3ClO_4$]: Ammonium-hexabromo-osmate (IV) is heated on the waterbath in the presence of sodium tartrate and 3 mole dipyridine. To isolate the complex, the reaction solution is mixed with perchloric acid, whereupon, the desired compound crystallizes out.

7. Complexes with gold (l) Trichloro-dipyridine gold [Au $(C_5H_5N)_2Cl_3$]: Pyridine is added in drops to an etheric gold-(III)-chloride solution, a yellow precipitate separating out immediately, which can be recrystallized from alcohol.

8. Complexes with silver (m) Silver-dipyridine-nitrate [Ag $(C_5H_5N)_2NO_3$]: An aqueous silver nitrate solution is mixed with an excess of pyridine and then precipitated with ether.

Other complex compounds can be produced in similar manner. Generally, the complex compounds are soluble in water. The compounds which are slightly soluble in water are soluble in aqueous soda or potash lye solutions, or in organic solvents, such as, methanol, ethanol or acetic acid.

The application of the activating solutions according to the invention is effected, for example, by simply immersing the materials to be activated in these solutions at temperatures of about 0° to 80° C., preferably 40° to 60° C. The duration of the activation process depends on the material to be activated and may be from about 0.5 to 20 minutes.

The materials treated with the activating solutions are then introduced into a reducing solution which reduces the precious metal ions to the metal. For this purpose suitable reducing agents, particularly dimethylaminoborane, sodium boronate, hydrazine and alkali hypophophite, e.g. sodium hypophosphite, are used.

With the solutions according to the invention, plastic surfaces with a base of acrylonitrile-butadiene-styrene polymers (ABS polymers), polypropylene, epoxide, glassfiber-reinforced epoxide, etc. or respectively support plates of this material can be activated for the subsequent chemical metallization. If in addition water-soluble polymeric organic compounds are admixed with the solutions, as described above, one obtains, surprisingly, even an increase of the adsorption of these complexes, which then, because of the greater affinity to the plastic, deposit on the surface thereof and not on the metal.

The solutions according to the invention are suitable for the activation of plastic moldings or, in particular, of copper-coated base material for the production of printed circuits.

DESCRIPTION OF THE PREFERRED EMBODIMENTS

The following examples preferably describe some of the activating solutions according to the invention, and their characteristics.

EXAMPLE 1

0.34 g $PdCl_2$
1.28 g pyridine-3-sulfonic acid filled up to 1 liter of water
pH of the solution: 2.2
adjusted to 7 with NaOH.

EXAMPLE 2

0.34 g $PdCl_2$
0.95 g 2-amino-pyridine filled up to 1 liter of water
pH of the solution: 6.4
Addition of 0.2 g soy protein.

EXAMPLE 3

0.34 g $PdCl_2$
0.14 g $NH_3$ filled up to 1 liter of water
pH of the solution: 7.0
Addition of 0.2 g soy protein.

EXAMPLE 4

0.28 g $AuCl_3$
0.62 g pyridine filled up to 1 liter of water
pH of the solution: 3.3
Adjusted to 7.0 with NaOH.

In the following example the activation of a non-conductor with the use of the solutions according to the invention is described.

EXAMPLE 5

The starting material was copper-coated base plates of phenol resin laminated paper or glassfiber reinforced epoxy resin. These plates were stamped or drilled in the sense of the later conductor pattern and cleaned or pickled according to known methods, to prepare the surface of the bore hole inside wall for the adsorption of the activator. After thorough rinsing in water, the material was immersed for 5 minutes at 60° C. in a solution of the composition according to example 1, again rinsed, and exposed for 1 to 3 minutes at 40° C. to the action of a reducing agent of sufficiently high reduction potential, such as an approximately 1% aqueous solution of sodium hypophosphite or dimethylaminoborane. Then the object was again rinsed in water and metallized without current in a chemical copper bath in the usual manner. There was thus formed the copper film growing from seeds of precious metal, which it was then possible to reinforce galvanically. In a similar manner copper coated base plates were treated with activating solutions according to the examples, 2, 3 and 4. The metal coatings thus obtained exhibited excellent conductivity and adhesivity.

What is claimed is:

1. An activating composition for preparing unactivated surfaces having a base of acrylonitrile-butadiene-styene-polymers, polypropylene, epoxide or glass-fiber-reinforced epoxide for chemical metallization, comprising an aqueous solution having a pH of between about 2.2 and 7 of a compound selected from the group consisting of dichloro-bis-(2-aminopyridine)-palladium-(II) and dichloro-tetrakis-(2-aminopyridine)-palladium-(II), wherein the concentration of palladium metal in said solution is between about 0.05 and 1 g/l.

2. A method for activating the unactivated surface of a synthetic organic polymer for chemical metallization, comprising applying to said surface which has not been chemically pretreated or previously activated an effective amount of the composition of claim 1.

* * * * *